United States Patent [19]
Slater et al.

[11] Patent Number: 5,522,883
[45] Date of Patent: Jun. 4, 1996

[54] ENDOPROSTHESIS STENT/GRAFT DEPLOYMENT SYSTEM

[75] Inventors: Andrea T. Slater, Hillsborough, N.J.; Brian P. Byrne, Middletown, N.Y.

[73] Assignee: Meadox Medicals, Inc., Oakland, N.J.

[21] Appl. No.: 390,049

[22] Filed: Feb. 17, 1995

[51] Int. Cl.⁶ .................................................. A61F 2/06
[52] U.S. Cl. .............................. 623/1; 606/108; 606/194; 606/198; 604/104
[58] Field of Search .................................. 623/1, 11, 12; 606/108, 191, 194, 195, 198; 604/96, 104, 281

[56] References Cited

U.S. PATENT DOCUMENTS

| | | | |
|---|---|---|---|
| 2,701,559 | 2/1955 | Cooper | 128/2 |
| 3,467,102 | 9/1969 | Fogarty et al. | 128/348 |
| 3,635,215 | 1/1972 | Shea et al. | 128/130 |
| 4,143,651 | 3/1979 | Patel | 128/349 |
| 4,300,244 | 11/1981 | Bokros | 3/1.4 |
| 4,732,152 | 2/1988 | Wallsten et al. | 128/343 |
| 4,787,899 | 11/1988 | Lazarus | 623/1 |
| 4,875,480 | 10/1989 | Imbert | 128/343 |
| 4,950,227 | 8/1990 | Savin et al. | 604/8 |
| 4,955,895 | 9/1990 | Sugiyama et al. | 606/194 |
| 5,078,720 | 1/1992 | Burton et al. | 606/108 |
| 5,108,416 | 4/1992 | Ryan et al. | 606/194 |
| 5,158,545 | 10/1992 | Trudell et al. | 604/53 |
| 5,158,548 | 10/1992 | Lau et al. | 604/96 |
| 5,190,058 | 2/1993 | Jones et al. | 128/898 |
| 5,226,889 | 7/1993 | Sheiban | 604/101 |
| 5,242,399 | 9/1993 | Lau et al. | 604/104 |
| 5,292,321 | 3/1994 | Lee | 606/28 |
| 5,295,961 | 3/1994 | Niederhauser et al. | 604/96 |
| 5,304,135 | 4/1994 | Shonk | 604/101 |
| 5,308,323 | 5/1994 | Sogawa et al. | 604/95 |
| 5,464,449 | 11/1995 | Ryan et al. | 606/191 |

*Primary Examiner*—Randy C. Shay
*Attorney, Agent, or Firm*—Hoffman & Baron

[57] ABSTRACT

A deployment system for transcutaneous insertion of an implantable tubular prosthesis is provided. The deployment system includes a flexible, elongated, tubular, delivery catheter with at least one inner lumen, and an opening extending through the catheter to the inner lumen. Positioned over the catheter is an implantable endoprosthesis capable of radial expansion and having a proximal and a distal end extent. A support assembly removably maintains the endoprosthesis in a compressed state, and is located at a position adjacent the catheter opening. The support assembly includes an arm which extends through the catheter opening into the inner lumen. A release mechanism is insertable through the inner lumen and includes a distal tip engageable with the arm of the support assembly. The release mechanism is manipulatable within the inner lumen so as to remove the support assembly from the endoprosthesis, permitting radial expansion of the endoprosthesis for implantation.

37 Claims, 2 Drawing Sheets

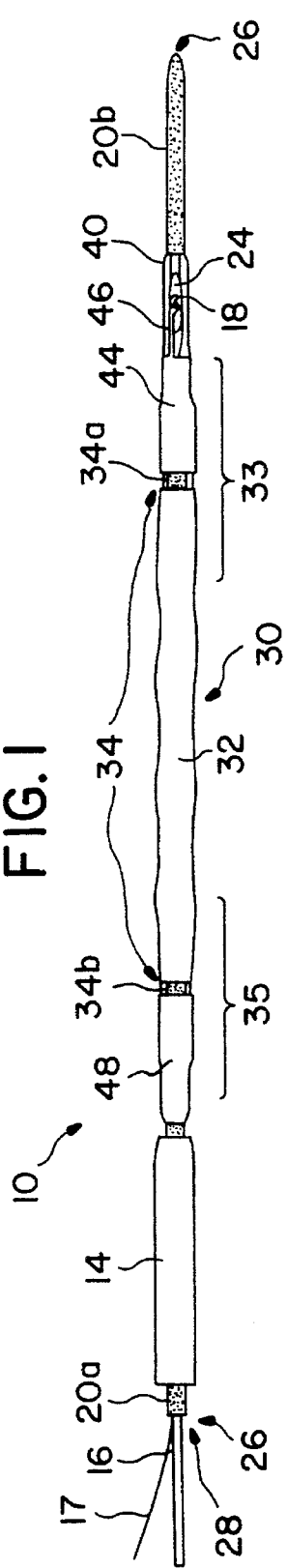
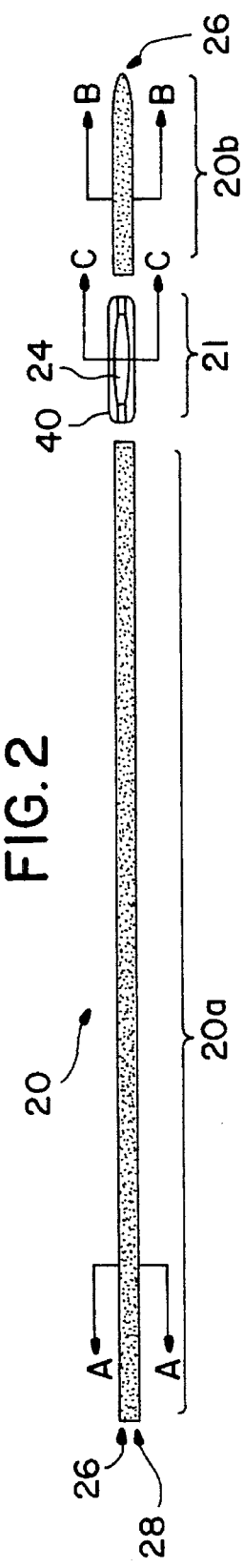
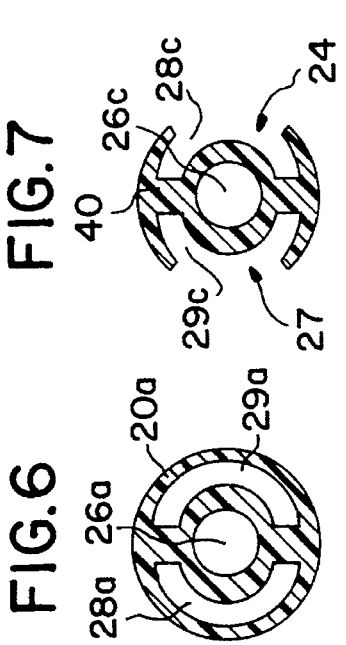
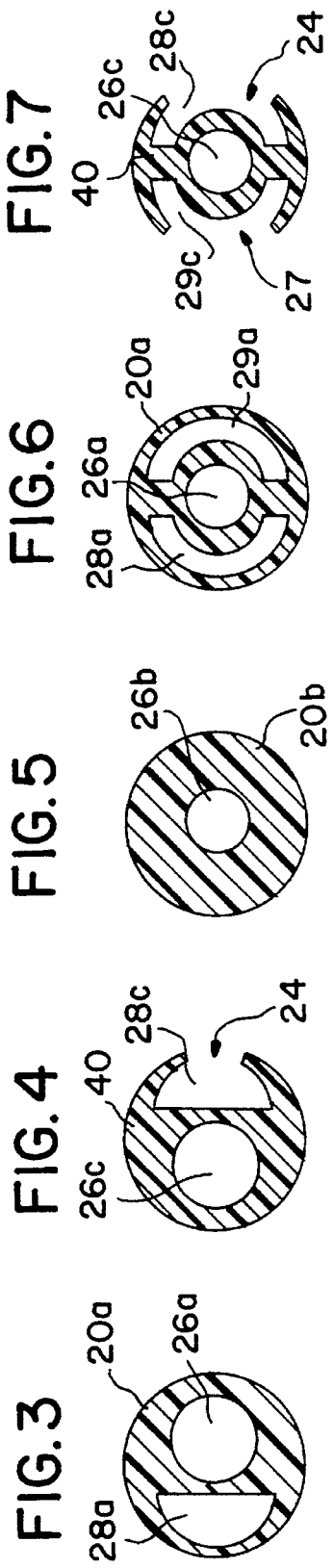

ENDOPROSTHESIS STENT/GRAFT DEPLOYMENT SYSTEM

FIELD OF THE INVENTION

The present invention relates generally to a deployment system for an implantable endoprosthesis. More particularly, the present invention relates to a deployment system for transcutaneous insertion of an implantable tubular prosthesis supported by a stent.

BACKGROUND OF THE INVENTION

The implantation of synthetic tubular prostheses to replace or buttress damaged or diseased vascular vessels or other luminal passageways within the human body is well known. Synthetic tubular prostheses include grafts as well as endoprosthetic devices.

Tubular prostheses such as grafts are most commonly implanted by surgical techniques. Typically, a surgeon sutures the graft in place within the blood vessel or other body passageway to be repaired in an open surgical technique. Intraluminal implantation is also a common technique for implanting tubular prostheses. This procedure typically involves percutaneous insertion of an endoprosthesis by way of a delivery catheter. This procedure permits delivery and implementation without the need for major surgical intervention and the risks inherent therewith. Thus, intraluminal implantation of various prosthetic devices via delivery catheters is becoming increasingly common.

With respect to grafts and other prostheses which may traditionally be surgically implanted, means other than suturing must be used to secure these prostheses in place within the body passageway in order to effectively permit intraluminal implantation. It is known to employ stents in combination with grafts and various other prostheses in order to support and secure such a device in place within the body passageway after implantation. Stents are typically radially expandable and/or contractible support members which are positioned within a graft or other tubular prosthesis. In common usage, after a prosthesis has been properly positioned, the stent is expanded to anchor the prosthesis within the body passageway.

Since a stent must be expanded to support the prosthesis within the body passageway for implantation, the delivery system used to transport the stent to the location of implantation must be capable of maintaining the stent in a compressed state during delivery and implantation until such time a stent deployment is necessitated. Attempts have been made to improve delivery systems for compressed stents. Several disclosures relate to such systems.

U.S. Pat. No. 4,950,227 discloses a catheter delivery system for a stent wherein the stent is positioned about a balloon-type catheter and held in position by a sleeve fixing the end of the stent. As the balloon is inflated, the stent is expanded, causing the sleeve to slide off of the stent and release the stent.

U.S. Pat. No. 5,108,416 discloses a catheter delivery system for a stent wherein the stent is positioned about a balloon type catheter and held in position by end caps. As the balloon is inflated, the end caps move away from the stent and release the stent.

U.S. Pat. Nos. 5,158,548 and 5,242,399 disclose a stent delivery system wherein a stent is positioned about a balloon-type catheter and held in position by an outer sheath. A guidewire attached to the outer sheath is moved forward, thereby moving the sheath forward to expose and release the stent.

Accordingly, a need exists for an effective system for catheter delivery and deployment of a stent-supported implantable tubular prosthesis.

SUMMARY OF THE INVENTION

It is an object of the present invention to provide a deployment system for an implantable endoprosthesis that is to be delivered transcutaneously.

It is a further object of the present invention to provide an improved deployment system which provides for the implantation of a radially expandable endoprosthesis.

It is a still further object of the invention to provide a method for endoprosthetic deployment of an implantable endoprosthesis.

In the attainment of these and other objects, the present invention provides a deployment system which includes a flexible, elongated, tubular, delivery catheter with at least one inner lumen, and an opening extending through the catheter to the inner lumen. Positioned over the catheter is an implantable endoprosthesis capable of radial expansion and having a proximal and a distal end extent. A support assembly removably maintains the endoprosthesis in a compressed state, and is located at a position adjacent the catheter opening. The support assembly includes an arm which extends through the catheter opening into the inner lumen. A release mechanism is insertable through the inner lumen and includes a distal tip engageable with the arm of the support assembly. The release mechanism is manipulatable within the inner lumen so as to remove the support assembly from the endoprosthesis, permitting radial expansion of the endoprosthesis for implantation.

The endoprosthesis is preferably a graft having an expandable stent for support, more particularly, a pair of expandable stents with one at the proximal end extent and one at the distal end extent. The support assembly is preferably a boot. The release mechanism may include a release rod, and may further include a clip at the distal tip which is capable of attachment to the arm.

The support assembly may include a distal support member, for maintaining the distal end extent of the endoprosthesis in a compressed state. A proximal support member anchored to the catheter may further be included for maintaining the proximal end extent of the endoprosthesis in a compressed state. The distal end extent and proximal end extent of the endoprosthesis may be separate members. In this embodiment, the distal support member maintains the distal endoprosthesis member and the proximal support member maintains the proximal endoprosthesis member.

The deployment system may further include a guidewire insertable through the inner lumen of the catheter. The catheter may further include a proximal portion and a distal portion. The proximal portion and distal portion of the catheter may be separate portions connected by a connector portion, with the opening through the catheter located at the connector portion.

The catheter may have a first and a second inner lumen, with the opening extending through to the first inner lumen, the release mechanism insertable through the first lumen, and the guidewire insertable through the second lumen.

In its method aspect, the present invention includes providing a deployment system including: a flexible elongated tubular delivery catheter having a proximal portion, a distal portion, at least one inner lumen, and an opening through the catheter to the inner lumen; an implantable endoprosthesis capable of radial expansion positioned over the catheter and having a proximal end extent and a distal end extent; a retractable endoprosthesis support assembly for removably maintaining the endoprosthesis in a compressed state located at a position adjacent the catheter opening and having an arm extending through the catheter opening into the lumen; and a release mechanism having a distal tip, insertible through the inner lumen, engageable with the arm, and capable of manipulation of the support assembly within the inner lumen. The deployment system is intraluminally inserted and positioned at an area of implantation. The release mechanism is then engaged with the arm of the support assembly, and the release mechanism is manipulated within the inner lumen. This manipulation removes the support assembly from the endoprosthesis and permits radial expansion of the endoprosthesis. The deployment system is then removed from the area of implantation.

BRIEF DESCRIPTION OF THE DRAWINGS

FIG. 1 is a perspective view of a preferred embodiment of the endoprosthetic deployment system of the present invention.

FIG. 2 is a side view of a delivery catheter assembly used in accordance with the present invention.

FIG. 3 is an enlarged cross-sectional view of the catheter assembly of FIG. 2 taken along line A—A thereof.

FIG. 4 is an enlarged cross-sectional view a component of the catheter of FIG. 2 taken along line C—C thereof.

FIG. 5 is an enlarged cross-sectional view of the catheter assembly of FIG. 2 taken along line B—B thereof.

FIG. 6 is an enlarged cross-sectional view of a further embodiment of the catheter assembly of FIG. 2 taken along line A—A.

FIG. 7 is an enlarged cross-sectional view of the alternative embodiment of FIG. 6 taken along line C—C of FIG. 2.

DETAILED DESCRIPTION OF THE INVENTION

Figure 8:
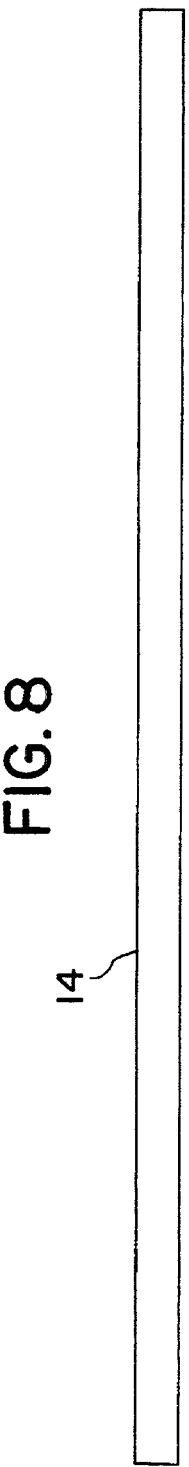
FIG. 8 is a side view of an outer sheath used in accordance with the present invention.

A deployment system 10 for transcutaneous insertion of an implantable endoprosthesis as contemplated by the present invention is shown in FIG. 1. Deployment system 10 includes a flexible elongated delivery catheter assembly 20. Catheter assembly 20 may be constructed of any generally flexible biocompatible material that is known in the art.

In preferred embodiments, catheter assembly 20 includes a proximal portion 20a and a distal portion 20b, as shown in FIG. 2. For the purposes of the present invention, "distal" is used to describe a general location of delivery system 10 that is first inserted into the body, while "proximal" is used to describe a general location of delivery system 10 that is opposite the distal portion. Proximal portion 20a and distal portion 20b are typically discrete portions, separated by discontinuity 21. In order to couple proximal portion 20a and distal portion 20b, a connector portion is employed, shown in FIGS. 1 and 2 as connector 40. Connector 40 is typically an elongated member having tapered ends for insertion within said proximal portion 20a and distal portion 20b at discontinuity 21, thereby coupling the two portions. Connector 40 may be constructed of a biocompatible material well known ill the art. When coupled together, proximal portion 20a, connector 40 and distal portion 20b effectively form a single catheter assembly 20.

Proximal portion 20a includes first inner lumen 26a and second inner lumen 28a extending therethrough, shown in FIG. 3. Distal portion 20b includes first inner lumen 26b extending therethrough, shown in FIG. 5. Connector 40 includes a first inner lumen 26c that communicates with first inner lumen 26a of proximal portion 20a, and further communicates with first inner lumen 26b of distal portion 20b. Connector 40 also includes a second inner lumen 28c that communicates with second inner lumen 28a of proximal portion 20a. With the proximal portion 20a, connector 40 and distal portion 20b coupled together, the communicating first inner lumens 26a, 26c and 26b effectively form a single first inner lumen 26 extending through catheter assembly 20, and communicating second inner lumens 28a and 28c form a single second inner lumen 28 extending through catheter assembly 20. First inner lumen 26 may accommodate a guidewire 17 therethrough. As is well known in the art, guidewires may be commonly used in catheter delivery systems to locate and guide a delivery catheter through the vascular system.

An opening 24 exists through the wall of connector 40, extending through to second inner lumen 28c, as depicted in FIG. 4. While the preferred embodiment of the invention includes connector 40, the present invention contemplates catheter assembly 20 as a single member catheter without connector 40, with such an embodiment including opening 24 through the wall of the single member catheter and extending through to inner lumen 28.

As can be seen in FIG. 1, an implantable endoprothesis 30 capable of radial expansion is positioned over catheter assembly 20. Endoprosthesis 30 includes a proximal end extent 35 and a distal end extent 33. Endoprosthesis 30, further shown in FIG. 10, may be any type of implantable prosthetic device known in the art. The present invention contemplates endoprosthesis 30 existing as a straight, tapered, stepped, bifurcated, or any other type of endoprosthesis useful in implantation procedures.

In preferred applications, endoprosthesis 30 includes a vascular graft 32, which may be constructed of braided, knitted, or woven synthetic yarns such as polyester, or may be formed of an extruded plastic such as expanded polytetraflouroethylene (PTFE). Graft 32 is designed for percutaneous implantation within a diseased or damaged blood vessel or other like vessel to provide replacement or reinforcement of the damaged vessel. In this regard, graft 32 is folded or compressed to facilitate intraluminal delivery. Such compression or folding is well known in the art, and the present invention contemplates the graft existing in any compressed or folded shape which would permit radial expansion.

Graft 32 may be a self-supporting-type graft known in the art, or may be supported by other means. For example, graft 32 may be supported by an expandable stent 34, further depicted in FIG. 10. Stent 34 may be any conventional stent constructed of any material known in the art, such as stainless steel or other metals or alloys, polymeric materials, or composites of polymers and metal. Stent 34 is self-expandable in a radial direction between a compressed diameter and a larger expanded diameter. Stent 34 may further contain stent barbs (not shown) extending therefrom, which are commonly used in stent applications for aiding in positioning and anchoring of endoprostheses.

Figure 10:
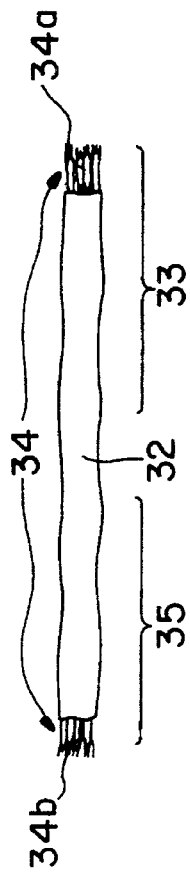
FIG. 10 is a perspective view of an endoprosthesis including a graft and stent of the type used with the delivery system of the present invention.

In preferred form, proximal end extent 35 and distal end extent 33 of endoprosthesis 30 support separate discrete stent members. This embodiment is particularly useful when endoprosthesis 30 includes a graft and stent combination. In such an embodiment, stent 34 may include two spaced-apart members, proximal stent member 34b and distal stent member 34a, as shown in FIG. 10. In such an embodiment, distal stent member 34a supports and anchors distal end extent 33 of graft 32 to the implantation area, while proximal stent member 34b supports and anchors proximal end extent 35 of graft 32 to the implantation area.

In order to captively retain endoprosthesis 30 in a compressed state prior to and during implantation, the present invention employs a removable endoprosthesis support assembly for removably maintaining endoprosthesis 30 in its compressed state. The support assembly may include a stent boot which maintains endoprosthesis 30 in a compressed state.

Figure 12:
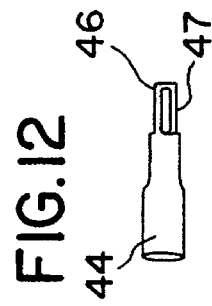
FIG. 12 is a perspective view of a distal support member used in accordance with the present invention.
Figure 11:
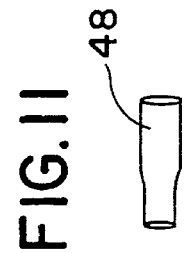
FIG. 11 is a perspective view of a proximal support member used in accordance with one embodiment of the present invention.

In preferred embodiments, the support assembly exists as two separate members. Referring to FIGS. 1, 11 and 12, the support assembly is shown as a distal support member 44 and a longitudinally spaced proximal support member 48. Spaced apart support members 44 and 48 are particularly useful where endoprosthesis 30 is a stent/graft combination as shown herein. Distal support member 44 surrounds and maintains distal end 33 in a compressed state, while proximal support member 48 surrounds and maintains proximal end extent 35 in a compressed state. Proximal support member 48 is anchored to catheter assembly 20 along proximal portion 20a. Adhesive or other fastening techniques may be employed.

Distal support member 44 is located at a position adjacent opening 24 of connector 40 of catheter assembly 20. Distal support member 44 includes an arm 46, which extends through opening 24 of connector 40 to second inner lumen 28c.

A release mechanism 16 having a distal tip 13 is insertable through second inner lumen 28 of catheter 20. Release mechanism 16 is retractably movable within catheter 20. Manipulation of the release mechanism contemplates any activity which would result in the removal of the support assembly. For instance, the release mechanism may be manipulated by movement within catheter 20 in an axial or longitudinal direction thereby engaging the support assembly, or the release mechanism may be manipulated by other means known in the art.

Figure 9:
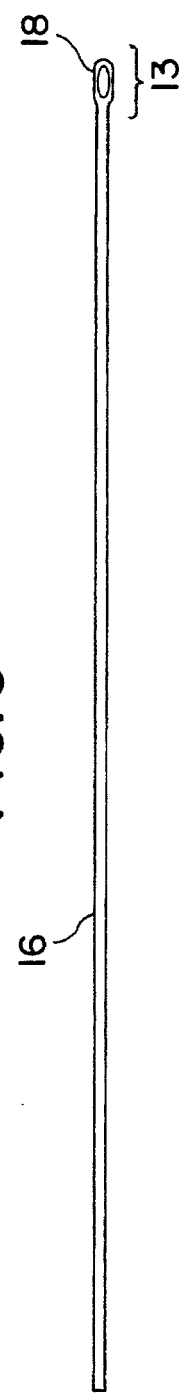
FIG. 9 is a side view of a release mechanism used in accordance with the present invention.

Release mechanism 16, shown in FIG. 9, may include a release rod, having a clip 18 at distal tip 13. Clip 18 is engagable with and capable of attachment to arm 46 of distal support member 44, which extends through opening 24 of connector 40. This attachment permits the removal of distal support member 44 from distal end 33 when release mechanism 16 is retractably moved by moving the release rod in a longitudinal direction toward the distal end of the deployment system 10.

As release mechanism 16 need only reach arm 46 extending through connector 40 at opening 24, it is not necessary for second inner lumen 28 to extend past connector 40 through distal portion 20b, although such a design is within the contemplation of the present invention.

In preferred applications, the deployment system of the present invention is utilized with minimally invasive transcutaneous insertion of an implantable endoprosthesis. More preferably, the deployment system of the present invention is utilized with percutaneous insertion of a stent supported vascular graft. However, it may be appreciated that the deployment system of the present invention may be utilized with any endoprosthetic implantation procedure, including transcutaneous implantation, percutaneous implantation, cut down procedures, and the like.

Having described the components of the present invention, use of the deployment system 16 may now be described. In this preferred application, a needle (not shown) is inserted intraluminally into a blood vessel (not shown). A guidewire 17 is then inserted through the needle and advanced through the blood vessel to the area of implantation. The deployment system 10 is then inserted into the blood vessel and guided over the guidewire inserted through inner lumen 26 to a position at the area of implantation.

After reaching the area of implantation, release mechanism 16 can be inserted through second inner lumen 28. Release mechanism 16 may also have been inserted into second inner lumen 28 prior to inserting deployment system 10 intraluminally. Clip 18 of release mechanism 16 engages distal support member 44 at arm 46, which extends through opening 24 at connector 40. After engaging at arm 46, release mechanism 16 is manipulated by moving release mechanism 16 within second inner lumen 28, in a longitudinal direction toward the distal end of deployment system 10. As clip 18 and arm 46 are engaged, movement of release mechanism 16 causes movement of distal support member 44, thereby removing distal support member 44 from its position maintaining distal stent member 34a in compressed state. With distal support member 44 removed, distal stent member 34a radially expands, and attaches distal end extent 33 of graft 32 to the inner wall of the vascular surface.

After distal stent member 34a fully expands, proximal support member 48, being anchored to proximal portion 20a of catheter assembly 20, still maintains proximal stent member 34b in a compressed state. Deployment system 10, including catheter assembly 20, is then removed from the area of implantation. As proximal support member 48 is anchored to proximal portion 20b, this removal causes proximal support member 48 to be removed from proximal stent member 34b. This removal permits radial expansion of proximal stent member 34b, thereby anchoring proximal end extent 35 of graft 32 to the vascular wall. With both ends of the vascular graft 32 now anchored, the graft is implanted, and deployment system 10 can be completely removed from the blood vessel.

The present invention further contemplates catheter assembly 20 existing as a single lumen catheter, with the guidewire and release mechanism 16 insertable through the single lumen. The present invention also contemplates catheter 20 assembly existing as a multiple lumen catheter, such as a triple lumen catheter as depicted in the cross-sectional view of FIGS. 6 and 7. In this alternate embodiment, proximal portion 20a of catheter assembly 20 has inner lumen 26a, second inner lumen 28a, and third inner lumen 29a. Also included in this embodiment is a second opening 27 through catheter 20 assembly at connector 40, extending through to third inner lumen 29c. Second opening 27 is at a point adjacent opening 24, but not connected with opening 24. In this embodiment, inner lumen 26 accepts a guidewire, second inner lumen 28 accepts release mechanism 16, and third inner lumen 29 can accept a second release mechanism (not shown). The second release mechanism can be identical to release mechanism 16. The second release mechanism is engaged with a second arm 47 which may be included with distal support member 44, as depicted in FIG. 12. Second arm 47 extends through catheter assembly 20 at opening 27 in a similar manner as arm 46 through opening 24. In this embodiment, release mechanism 16 engages arm 46 while second release mechanism engages second arm 47, thereby permitting removal of distal support member 44 when both the first and second release mechanisms are moved.

In yet another embodiment of the invention, catheter assembly 20 exists as a three-lumen catheter similar to that described above, with the third lumen capable of accommodating a second release mechanism engaged with the proximal support member. In this embodiment, a second opening exists through catheter assembly 20 adjacent the proximal support member. The proximal support member includes an arm which extends through this second opening of the catheter assembly in a similar manner as arm 46 extends through opening 24 of the preferred embodiment. In this alternate embodiment, the second release mechanism engages the arm of the proximal support member and manipulation of the second release mechanism causes the proximal support member to be removed from its position maintaining the proximal and extent of the endoprosthesis.

Alternatively, the third lumen may be used for other purposes, such as dye injection, drug infusion, and other known uses for catheter lumens. Additionally, whether a single lumen or multi-lumen catheter assembly, the shape of the lumen is not significant to the invention, so long as the shape does not preclude the lumen from performing the function intended.

The present invention also contemplates a retractible outer sheath 14, shown in FIG. 7, disposed over catheter assembly 20 and endoprosthesis 30, further maintaining endoprosthesis 30 in a compressed state and in position. Outer sheath 14 may be constructed of any flexible, biocompatible material known in the art. Outer sheath 14 is retractible after transcutaneous insertion, to permit exposure of endoprosthesis 30 to the surface of implantation. Outer sheath 14 is shown in FIG. 1 in its retracted state.

While the invention has been described herein in terms of certain preferred embodiments, those skilled in the art will recognize that various modifications can be made without departing from the scope of the present invention.

What is claimed is:

1. An implantable endoprosthesis deployment system comprising:

a flexible elongated tubular delivery catheter, said catheter having an inner lumen extending therethrough and an opening through said catheter in communication with said inner lumen;

an elongated implantable radially expandable endoprosthesis positioned over said catheter, said endoprosthesis having a proximal end extent and an opposed distal end extent;

a removable endoprosthesis support assembly for maintaining said endoprosthesis in a compressed state, said support assembly being located adjacent said catheter opening, said support assembly including an arm extending through said catheter opening into said inner lumen; and a release mechanism insertable through said inner lumen of said catheter, said release mechanism including a distal tip engageable with said arm of said support assembly, said release mechanism being manipulatable within said inner lumen so as to remove said support assembly from said endoprosthesis, permitting subsequent radial expansion of said endoprosthesis.

2. A deployment system as in claim 1, wherein said endoprosthesis includes a vascular graft.

3. A deployment system as in claim 2, wherein said endoprosthesis includes a stent.

4. A deployment system as in claim 1, wherein said support assembly includes a boot.

5. A deployment system as in claim 1, wherein said support assembly includes a distal support member maintaining said distal end extent of said endoprosthesis in a compressed state.

6. A deployment system as in claim 5, further comprising a proximal support member for removably maintaining said proximal end extent of said endoprosthesis in a compressed state, said proximal support member being anchored to said catheter.

7. A deployment system as in claim 6, wherein said proximal end extent and said distal end extent of said endoprosthesis are separate members.

8. A deployment system as in claim 1, wherein said release mechanism includes a release rod.

9. A deployment system as in claim 1, wherein said release mechanism includes a clip at said distal tip, said clip capable of attachment to said arm.

10. A deployment system as in claim 1, wherein said catheter includes a proximal portion and a distal portion.

11. A deployment system as in claim 10, wherein said proximal portion and said distal portion of said catheter are separate portions connected by a connector portion.

12. A deployment system as in claim 11, wherein said opening through said catheter is through said connector portion.

13. A deployment system as in claim 1, further comprising a guidewire insertable through said inner lumen.

14. A deployment system as in claim 1, wherein said catheter includes a first inner lumen and a second inner lumen.

15. A deployment system as in claim 14, wherein said opening extends through to said first inner lumen, said release mechanism is insertable through said first lumen, and said guidewire is insertable through said second lumen.

16. A deployment system as in claim 1, further comprising a retractible outer sheath disposed over said catheter, said sheath further maintaining said endoprosthesis in a compressed state.

17. A method of endoprosthetic deployment comprising:

a. providing a deployment system comprising a flexible elongated tubular delivery catheter, said catheter having an inner lumen extending therethrough and an opening through said catheter in communication with said inner lumen; an elongated implantable radially expandable endoprosthesis positioned over said catheter, said endoprosthesis having a proximal end extent and an opposed distal end extent; a removable endoprosthesis support assembly for maintaining said endoprosthesis in a compressed state, said support assembly being located adjacent said catheter opening and said support assembly including an arm extending through said catheter opening into said inner lumen; and a release mechanism insertable through said inner lumen of said catheter, said release mechanism including a distal tip engageable with said arm of said support assembly, said release mechanism being manipulatable within said inner lumen so as to remove said support assembly from said endoprosthesis, permitting subsequent radial expansion of said endoprosthesis;

b. inserting said deployment system intraluminally;

c. positioning said deployment system at an area of implantation;

d. engaging said release mechanism with said arm of said support member;

e. manipulating said release mechanism within said inner lumen, thereby removing said support member from said endoprosthesis and permitting radial expansion thereof; and f. removing said deployment system from said area of implantation.

18. A method as in claim 17, wherein said providing step a. further includes providing said support assembly including a distal support member for maintaining said distal end extent of said endoprosthesis in a compressed state.

19. A method as in claim 18, further comprising providing a proximal support member for removably maintaining said proximal end extent of said endoprosthesis in a compressed state, said proximal support member being anchored to said catheter.

20. A method as in claim 19, wherein said removing step e. removes said distal support member, thereby permitting radial expansion of said distal end extent of said endoprosthesis.

21. A method as in claim 17, wherein said providing step a. further includes providing said proximal end extent and said distal end extent of said endoprosthesis as separate members.

22. A deployment system as in claim 17, comprising providing a retractible outer sheath disposed over said catheter.

23. A deployment system as in claim 22, further comprising the step of retracting said outer sheath after said positioning step c.

24. A stent-prosthesis deployment system comprising:

a flexible elongated tubular delivery catheter having a proximal portion, a distal portion, an inner lumen, and an opening through said catheter in communication with said inner lumen;

an implantable prosthesis positioned over said catheter;

a radially expandable stent supporting said prosthesis, said stent having a proximal end extent and an opposed distal end extent;

a removable endoprosthesis support assembly for maintaining said stent in a compressed state, said support assembly being located adjacent said catheter opening, said support assembly further including an arm extending through said catheter opening into said inner lumen; and a release mechanism insertable through said inner lumen of said catheter, said release mechanism including a distal tip engageable with said arm of said support assembly, said release mechanism being manipulatable within said inner lumen so as to remove said support assembly from said stent, permitting subsequent radial expansion of said stent.

25. A deployment system as in claim 24, wherein said prosthesis includes a vascular graft.

26. A deployment system as in claim 24, wherein said support assembly includes a boot.

27. A deployment system as in claim 24, wherein said support assembly includes a distal support member maintaining said distal end extent of said stent in a compressed state.

28. A deployment system as in claim 27, further comprising a proximal support member for removably maintaining said proximal end extent of said stent in a compressed state.

29. A deployment system as in claim 24, wherein said proximal end extent and said distal end extent of said stent are separate members.

30. A deployment system as in claim 24, wherein said release mechanism includes a release rod.

31. A deployment system as in claim 24, wherein said release mechanism includes a clip, said clip capable of attachment to said arm.

32. A deployment system as in claim 24, wherein said proximal portion and said distal portion of said catheter are separate portions connected by a connector portion.

33. A deployment system as in claim 32, wherein said opening through said catheter is through said connector portion.

34. A deployment system as in claim 24, further comprising a guidewire insertable through said inner lumen.

35. A deployment system as in claim 24, wherein said catheter includes a first inner lumen and a second inner lumen.

36. A deployment system as in claim 24, wherein said opening extends through to said first inner lumen, said release mechanism is insertable through said first lumen, and said guidewire is insertable through said second lumen.

37. A deployment system as in claim 24, further comprising a retractible outer sheath disposed over said catheter.

* * * * *

UNITED STATES PATENT AND TRADEMARK OFFICE
CERTIFICATE OF CORRECTION

PATENT NO. : 5,522,883
DATED : June 4, 1996
INVENTOR(S) : Slater, et. al.

It is certified that error appears in the above-indentified patent and that said Letters Patent is hereby corrected as shown below:

Column 4, line 11, should read--well known in the art--.

Signed and Sealed this

Twenty-fourth Day of September, 1996

Attest:

BRUCE LEHMAN

Attesting Officer　　　Commissioner of Patents and Trademarks